United States Patent
Lai et al.

(10) Patent No.: US 6,919,571 B2
(45) Date of Patent: Jul. 19, 2005

(54) MICRO FLUORESCENT ELECTROPHORESIS DETECTION SYSTEM

(75) Inventors: Pong Lai, Taipei Hsien (TW); Ying-Tsung Lu, Kaohsiung (TW); Hoang-Yan Lin, Keelung (TW)

(73) Assignee: Industrial Technology Research Institute, Hsinchu Hsien (TW)

( * ) Notice: Subject to any disclaimer, the term of this patent is extended or adjusted under 35 U.S.C. 154(b) by 144 days.

(21) Appl. No.: 10/336,734

(22) Filed: Jan. 6, 2003

(65) Prior Publication Data

US 2004/0041098 A1 Mar. 4, 2004

(30) Foreign Application Priority Data

Sep. 4, 2002 (TW) .......................... 91120142 A

(51) Int. Cl.$^7$ ............................................. G01N 21/64
(52) U.S. Cl. ................................................. 250/458.1
(58) Field of Search ......................... 250/458.1, 459.1, 250/461.1, 461.2

(56) References Cited

U.S. PATENT DOCUMENTS

| | | |
|---|---|---|
| 5,556,529 A | 9/1996 | Nemoto |
| 5,885,430 A | 3/1999 | Kernan et al. |
| 5,993,634 A | 11/1999 | Simpson et al. |
| 6,039,925 A * | 3/2000 | Nemoto ................... 250/458.1 |
| 2002/0066866 A1 * | 6/2002 | Ogura ...................... 250/458.1 |

FOREIGN PATENT DOCUMENTS

JP          01-148946 A      12/1989

* cited by examiner

*Primary Examiner*—Constantine Hannaher
(74) *Attorney, Agent, or Firm*—Birch, Stewart, Kolasch & Birch, LLP

(57) ABSTRACT

A micro fluorescent electrophoresis (EP) detection system for detecting fluorescent EP is disclosed. The size of the system is greatly minimized for carrying. The invention uses a laser diode with a cylindrical lens to perform light source detection. A probe is provided to receive excited light produced by the probed object and to convert it into an electronic signal for detection. This does not only lower the cost, but also largely reduce its size for the patient's convenience of carrying and self-testing.

9 Claims, 3 Drawing Sheets

MICRO FLUORESCENT ELECTROPHORESIS DETECTION SYSTEM

This nonprovisional application claims priority under 35 U.S.C. § 119(a) on Patent Application No. 091120142 filed in TAIWAN, R.O.C. on Sep. 4, 2002, which is herein incorporated by reference.

BACKGROUND OF THE INVENTION

1. Field of Invention

The invention relates to an electrophoresis (EP) detection system for detecting fluorescent EP and, in particular, to a cost-effective micro fluorescent EP detection system of a small size for the convenience of carrying.

2. Related Art

Due to its ionization or charged particles attached thereon, any substance in an electric field will move toward a specific pole. The charged particles may be small ions or large biological molecules such as proteins, nucleus acid, viruses, or cells. The amino acid units that make up a protein are bipolar objects, which can be ionized and become a charge source under a certain pH environment. Charged particles under an electric field move toward the pole with the opposite polarity. This phenomenon is called electrophoresis (EP). In 1937, a Sweden scientist Tiselius invented the first EP device in the world and established the moving boundary EP method. Since there is a density change and therefore convection in the heated free solution in the moving boundary EP method, the initial region is disturbed and hard to distinguish. Moreover, the EP device is very expensive and it is hard to make it popular. In 1950s, people haven been improving the EP device and searching for better filter papers, cellulose acetate membranes, starch and agarose as the supporting mediator. In 1960s, polyacrylamide is found to be the supporting mediator and scientists had developed SDS-polyacrylamide EP, equal-potential EP, two-way EP, and print transfer EP techniques. These techniques have the advantages of simple equipment, convenient operations, and high distinction abilities. Currently, the EP technique has become an indispensable tool for biochemistry, immunology, molecular biology, and closely related medical sciences, agriculture, pharmacology and certain engineering analyses.

For example, the U.S. Pat. No. 5,885,430, "Capillary tube holder for an electrophoretic apparatus," utilizes the electric field strength change to increase of decrease the density of a probed solution. A laser beam is then shined on the probed solution to excite its fluorescent reaction. Such reaction information is then collected and processed to send out a signal for further analysis. However, its light-emitting part and the light-receiving part are not integrated. Not only does the system volume become too large, using laser as the light source is also very power consuming. It is almost impossible to meet the market demand for a compact device and the environmentally friendly consideration. Furthermore, the signal processing is very complicated. Its data analysis is quite time-consuming and thus lowers the detection efficiency.

SUMMARY OF THE INVENTION

To solve the above problems, the invention provides a micro fluorescent EP detection system. It does not only have a lower cost but also a small volume for the convenience of carrying. The power consumption is also lowered, while the detection efficiency is increased.

The disclosed micro fluorescent EP detection system includes a light source, a cylindrical lens, and a light receiver. The light source produces an excited light. One may use, for example, a laser diode that is cheap in cost to produce a monotonic beam. The cylindrical lens is installed in front of the light source to simultaneously produce multiple beams for several objects to be tested. The excited light from these probed objects is then taken for comparison.

The light receiver receives the excited light produced by the probed objects and provides analysis. It can include a filter installed in front of a probe. The filter allows only light with a particular excited wavelength to pass. The probe then receives the filtered beam and converts it into an electronic signal for detection. This method can greatly increase the detection efficiency. The light receiver is installed on one side of the light source, so that the light emission and reception are done one the same side of the device. This can greatly reduce the size of the system down to that of a palm or smaller. It is then extremely convenient for carrying.

BRIEF DESCRIPTION OF THE DRAWINGS

The invention will become more fully understood from the detailed description given hereinbelow illustration only, and thus are not limitative of the present invention, and wherein.

DETAILED DESCRIPTION OF THE INVENTION

Figure 2:
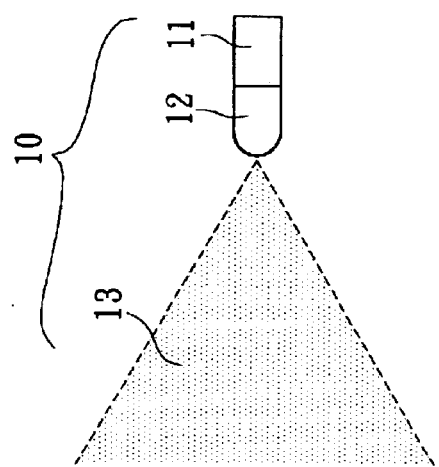
FIG. 2 is a schematic view of the light beam from the light source and passing through the cylindrical lens.
Figure 1:
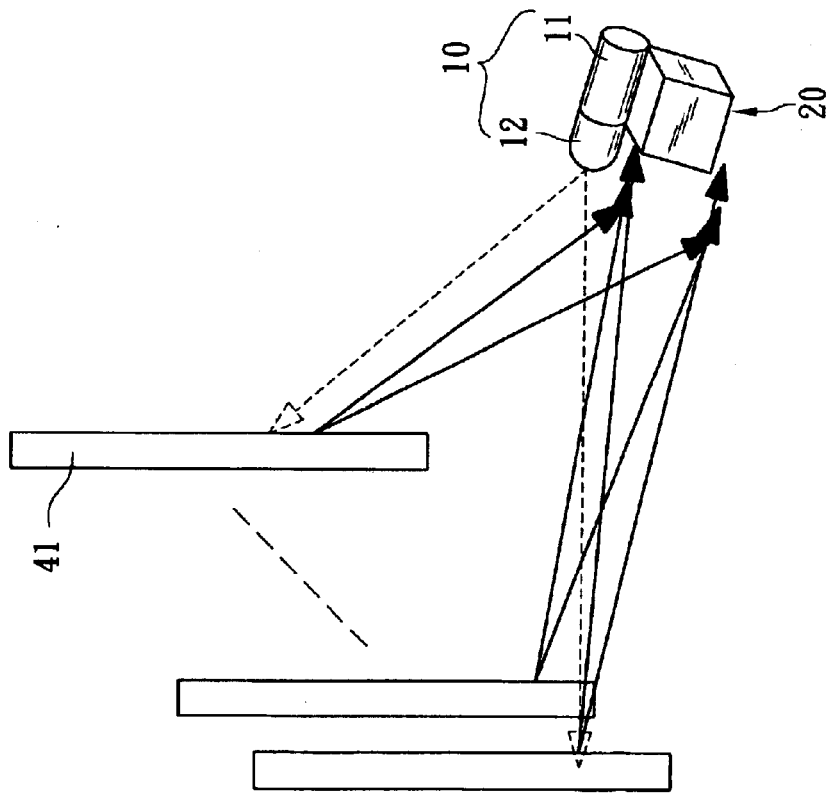
FIG. 1 shows the structure of the disclosed detection system.

With reference to FIG. 1, the disclosed micro fluorescent electrophoresis (EP) detection system is used to detect the EP of the probed object 41 in an electric field. A light beam is shined on an object 41 to be probed, and the invention measures the excited photon from the probed object 41 to detect the EP. The micro fluorescent EP detection system according to the invention contains a light source 10 and a light receiver 20. The light source 10 provides light to be shined on the probed object 41. It contains a laser diode 11 and a cylindrical lens 12, as shown in FIG. 2. Using the cheap and small laser diode 11 as the light source can lower the cost and volume of the system. The cylindrical lens 12 is installed in front of the laser diode 11. The laser diode 111 emits a light beam with a monotonic wavelength. After the cylindrical lens, a laser beam 13 is produced to simultaneously form several light spots along a line segment. In contrast, in the U.S. Pat. No. 5,885,430, the light spots do not simultaneously exist. It is therefore hard to compare the chemical reactions when several objects are measured at the same time.

Figure 3:
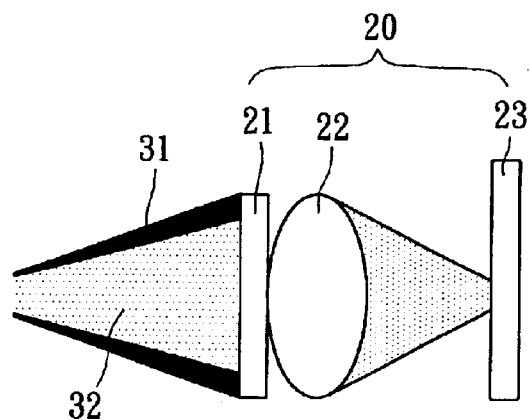
FIG. 3 is a schematic view of the light receiver.

Using the combination of a monotonic laser diode 11 and a cylindrical lens 12, the light spots formed by the laser beam 13 exist at the same time (FIG. 2). Thus, the invention can simultaneously shine the laser beam on several objects 41 to be probed (see FIG. 1), and compare the excited light from the objects. The light receiver 20 is installed on one side of the light source 10 for receiving the excited light from the probed objects 41 being shined by the laser beam 13. The received excited light is then used for detecting the EP of the probed objects 41. With reference to FIG. 3, the light receiver 20 contains a filter 21, a lens 22, and a probe 23. Since the light from the probed objects 41 includes both the reflected laser light 31 and the excited light 32, directly analyzing the entire light will affect the detection of fluorescent signals because the reflected light is stronger than the fluorescent light by a factor of three. Therefore, we use the filter 21 to remove the reflected laser light 31, allowing only the excited light to pass. After the laser light 32 passes the filter 21, the lens 22 converges the excited light 32 into the probe 23 for the convenience of detection. This can increase the detection efficiency. The probe 23 can be a charge-coupled device (CCD). The received photon energy is converted into electronic signals for subsequent processing and analyses.

Figure 4:
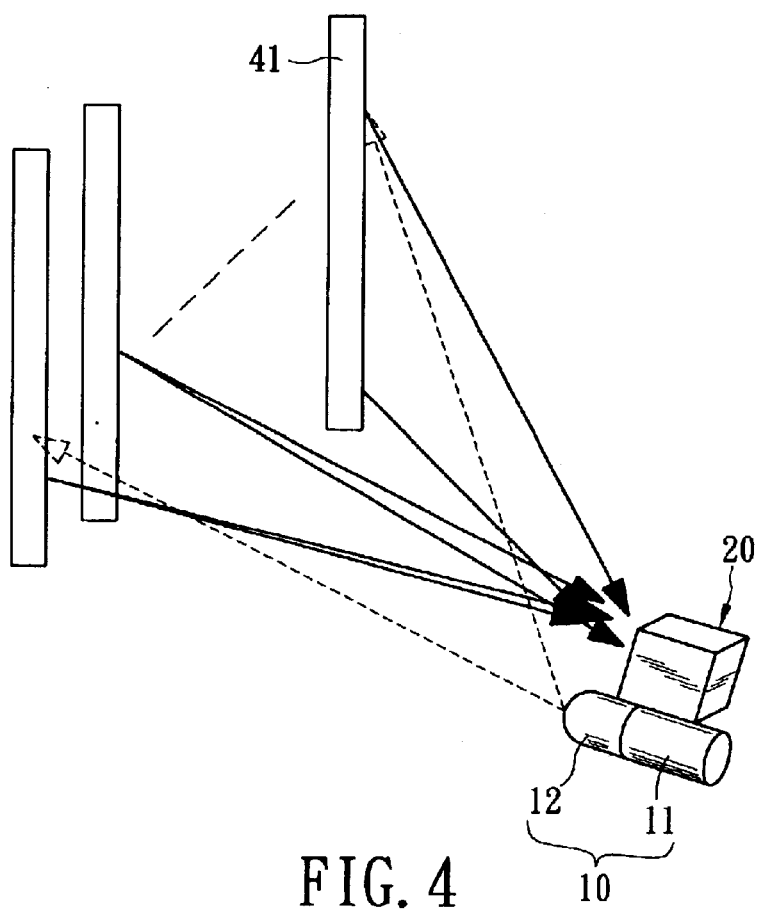
FIG. 4 is shows the structure of a second embodiment of the disclosed detection system.
Figure 5:
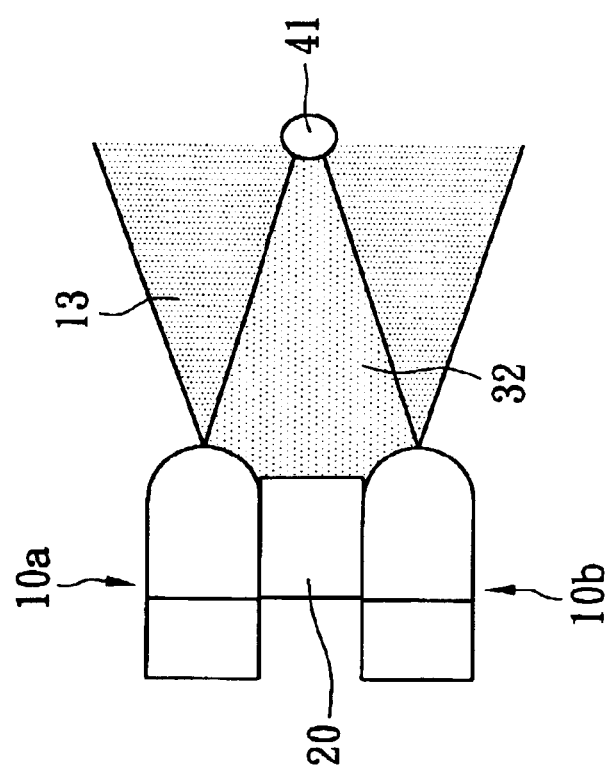
FIG. 5 is shows the structure of a third embodiment of the disclosed detection system.

To minimize the volume of the fluorescent EP detection system, the light receiver 20 is installed on the same side of the light source 10, such as the lower side (FIG. 1) or the upper side (FIG. 4). In the U.S. Pat. No. 5,885,430, the laser and the CCD are separated by a distance, making the volume of the system too large. On the other hand, one may also pair a single light receiver 20 with two light sources (the first light source 10a and the second light source 10b). As shown in FIG. 5, the first light source 10a and the second light source 10b are installed symmetrically on the left and right sides of the light receiver for detecting more objects 41.

EFFECTS OF THE INVENTION

The invention is a micro fluorescent EP detection system. The system uses a laser diode and a cylindrical lens as the light source. This configuration does not only lower the manufacturing cost, the light spots formed by the laser beam passing through the cylindrical lens are existent simultaneously for probing several objects at the same time. The light receiver is directly installed on one side or around the light source, so that the system is minimized in size for the convenience of carrying. Moreover, the light receiver has a filter and a lens in front of a CCD. The filter only allows the excited light to pass through. The lens then converges the excited light into the CCD, increasing the detection efficiency.

What is claimed is:

1. A micro fluorescent electrophoresis (EP) detection system for simultaneously detecting a plurality of objects placed in an electric field, the detection system comprising:
   a light source;
   a cylindrical lens disposed in front of the light source to produce a plurality of simultaneously existing scan beams to be shined on the objects; and
   a light receiver disposed on the light source, the light receiver receiving excited light produced by the probed objects being shined by the scan beams, the light receiver comprising:
      a filter receiving the excited light and allowing only the excited light to pass through; and
      a probe installed behind the filter for receiving the filtered excited light and converting the filtered excited light into an electronic signal.

2. The micro fluorescent EP detection system of claim 1, wherein the light source is one with a monotonic wavelength.

3. The micro fluorescent EP detection system of claim 2, wherein the light source is a laser diode.

4. The micro fluorescent EP detection system of claim 1, wherein the cylindrical lens is a half cylindrical lens.

5. The micro fluorescent EP detection system of claim 1, wherein the probe is a charge-coupled device (CCD).

6. The micro fluorescent EP detection system of claim 1, wherein the light receiver further contains a lens installed between the filter and the probe for converging the excited light into the probe.

7. The micro fluorescent EP detection system of claim 1, further comprising a plurality of light sources with their associated cylindrical lenses that are installed around the light receiver.

8. The micro fluorescent EP detection system of claim 1, wherein the light receiver directly contacts the light source.

9. The micro fluorescent EP detection system of claim 1, wherein a longitudinal axis of the light source is generally parallel to a longitudinal axis of the light receiver.

* * * * *